(12) United States Patent
Seah et al.

(10) Patent No.: US 7,154,661 B2
(45) Date of Patent: Dec. 26, 2006

(54) METHOD AND APPARATUS FOR IMAGING LATENT FINGERPRINTS

(75) Inventors: Leong Keey Seah, Singapore (SG); Murukeshan Vadake Matham, Singapore (SG); Lin Seng Ong, Singapore (SG); Zhixia Chao, Singapore (SG); Dinish Unnimadhava Kurup Soudamini Amma, Singapore (SG); Sock Koon Ong, Singapore (SG)

(73) Assignee: Nanyang Technological University, Singapore (SG)

( * ) Notice: Subject to any disclaimer, the term of this patent is extended or adjusted under 35 U.S.C. 154(b) by 35 days.

(21) Appl. No.: 11/023,170

(22) Filed: Dec. 27, 2004

(65) Prior Publication Data

US 2006/0114549 A1 Jun. 1, 2006

(30) Foreign Application Priority Data

Dec. 29, 2003 (SG) .............................. 200307736

(51) Int. Cl.
*G02F 2/02* (2006.01)
*G06K 9/20* (2006.01)

(52) U.S. Cl. ...................... 359/326; 382/124
(58) Field of Classification Search ................ 359/326; 382/124; 250/459.1
See application file for complete search history.

(56) References Cited

U.S. PATENT DOCUMENTS 6,306,662 B1 * 10/2001 Menzel ........................ 436/172
2002/0020818 A1 * 2/2002 Mitchell et al. ......... 250/459.1

OTHER PUBLICATIONS

E. Roland Menzel; Recent Advances in Photoluminescence Detection of Fingerprints; The Scientifice World; 2001; 1, 498-509.
B.E. Dalrymple, et al.; Inherent Fingerprint Luminescence—Dectection by Laser; Journal of Forensic Sciences; vol. 21; 1976; pp. 106-115.

* cited by examiner

*Primary Examiner*—John D. Lee
(74) *Attorney, Agent, or Firm*—Dinsmore & Shohl LLP

(57) ABSTRACT

The present invention relates to a method and apparatus for clearly imaging samples such as fingerprints on substrates of forensic samples. The present invention overcomes the problems of the Laser-Induced-Fluorescence (LIF) technique to distinguish fluorescence from the sample from that of the substrate. The method of the present invention uses either a homodyne- or a heterodyne-assisted phase resolving method, or both, to suppress the contribution of the substrate fluorescence. The resulting image of the sample will then be sufficiently clear for forensic purposes. The present invention may also be used on histological and biochemical samples to visualise latent images.

23 Claims, 9 Drawing Sheets

Fig. 6
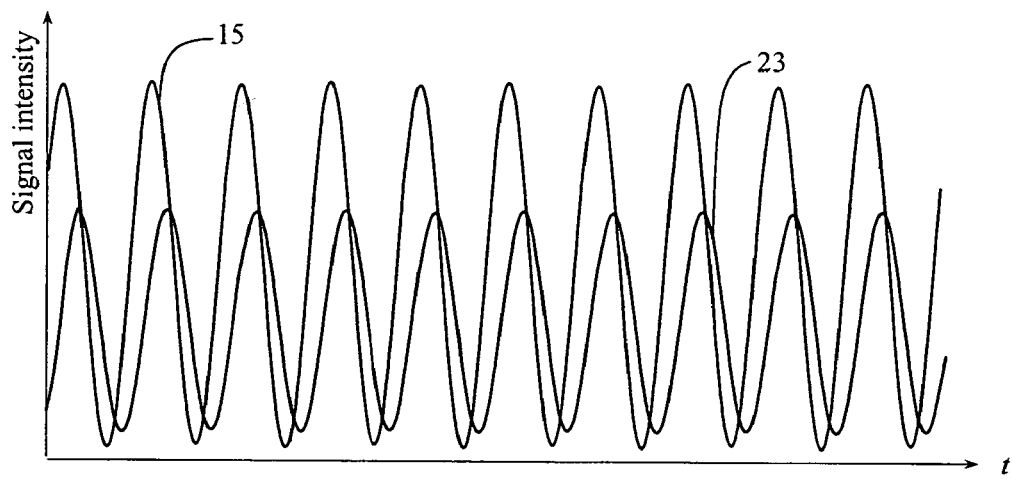
Fig. 6A
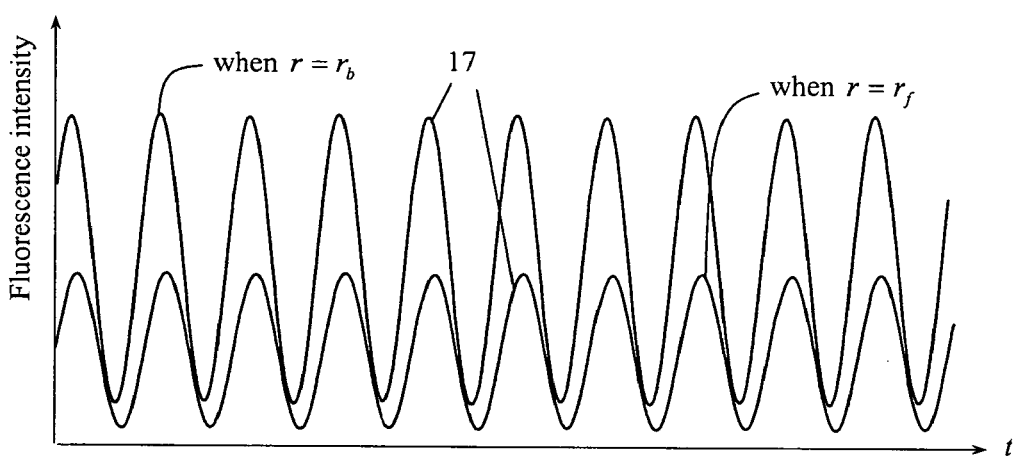
Fig. 6B
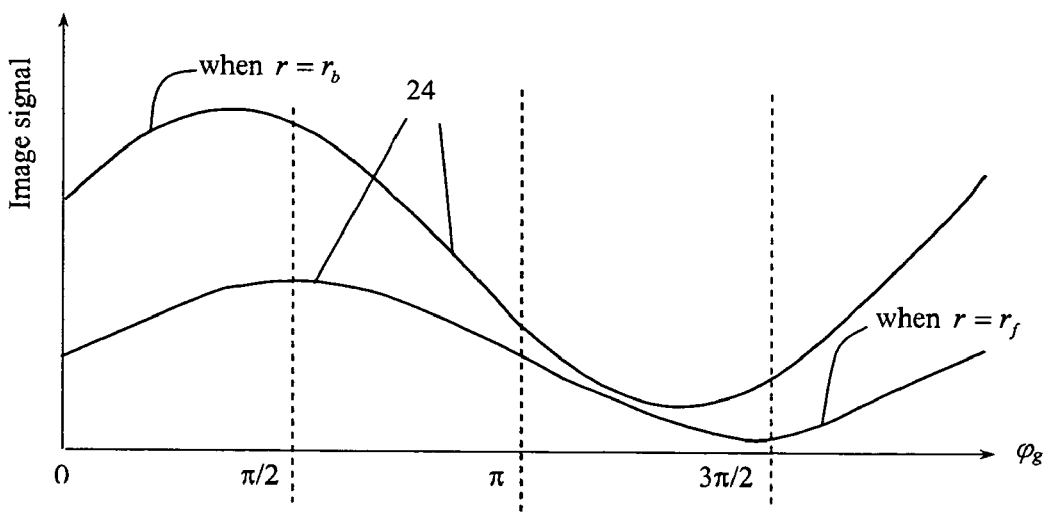
Fig. 6C

METHOD AND APPARATUS FOR IMAGING LATENT FINGERPRINTS

FIELD OF THE INVENTION

The present invention relates to methods and an apparatus for visualising images of a sample on a substrate.

In particular, the present invention relates to methods and an apparatus for visualising images of latent fingerprints for forensic purposes.

BACKGROUND OF THE INVENTION

Photoluminescence is often referred to as fluorescence and fluorescence is the emission of light from fluorescent materials. Fluorescent materials contain luminescent atoms or molecules, which can go into an excited state by absorbing electromagnetic erergy from an external source, which can come in the form of light. This electromagnetic energy, after being absorbed, is then released by the luminescent atoms or molecules, in the form of light. The emission of light from a fluorescent material is thus known as fluorescence. The imaging of latent fingerprints through fluorescence is one use of this phenomenon.

Whenever a finger touches a surface or substrate, it leaves a residue behind. This residue is mainly composed of water, which dries up eventually, leaving behind both inorganic salts and organic constituents. The pattern of deposition of this residue forms distinctive fingerprints that are unique to each individual. As some of these compounds are fluorescent, forensic scientists can use photoluminescent techniques to visualise fingerprints. Laser Induced Fluorescence (LIF) detection of fingerprints was demonstrated Dalrymple et alis in 1976 (Dalrymple et al "Inherent fingerprint luminescence—detection by laser," Journal of Forensic Sciences, Vol. 21, 1976, pp: 106–115). In that technique, optical filters were used to differentiate the fingerprint fluorescence from the substrate fluorescence, on the differences in intensity and colour of the fingerprint and substrate fluorescence. However, LIF detection of fingerprints using optical filters is fraught with problems when the substrate material fluoresce at a colour similar to that of the fingerprint fluorescence.

To overcome this problem, a new method uses the lifetime property of fluorescence to differentiate between the fingerprint and substrate fluorescence (Menzel, 2001). This method, the time resolved method, differentiates between the fingerprint fluorescence and the substrate fluorescence based on the lifetimes of each fluorescence source as opposed to simply differentiating between the colour and intensity.

As such, the time resolved method is able to image fingerprints that were once difficult to visualise. However, the time resolved method has two main limitations. This technique requires a large difference in fluorescence lifetimes between the different fluorescences in order to filter one fluorescence from the other. Furthermore, in order for time resolved method to work, the fingerprint fluorescence lifetime has to be longer than that of the substrate. Consequently, the time resolved method is only able to image fingerprints from a restricted range of substrates.

A technique that is able to discern fingerprints from a larger range of substrates is the phase resolved method, which makes use of the phase difference between the fluorescence of the fingerprint and the substrate when excited by a modulated illumination source. The advantage of using phase resolved method for fingerprint detection is that the fluorescence lifetime is no longer a consideration. Although phase resolved method is now being used in applications such as fluorescence microscopy and imaging of thick tissue, it has not been used in latent fingerprint detection due to the difficulties encountered.

The phase resolved method requires the fingerprint and the substrate to be excited to fluoresce by an illumination source that is modulated at a high frequency. This high frequency modulation, which can be of the order of several ten megahertz (MHz), is required in order to obtain a measurable phase difference to successfully suppress substrate fluorescence. However, it is difficult to carry out signal processing at such high frequencies since the image capturing devices are unable to respond to such high frequencies.

Another difficulty encountered in the use of the phase-resolved method for imaging fingerprints is that fingerprint fluorescence is too weak to be effectively detected by common detectors. As the substrate fluorescence may be strong compared to the fingerprint fluorescence, it can be difficult to suppress unwanted fluorescence components when imaging fingerprint samples. Therefore, although phase resolved method has proven useful in other applications, this method is not used in fingerprint fluorescence imaging as this method is currently unable to consistently obtain clear images of fingerprints from fingerprint samples.

SUMMARY OF THE INVENTION

In one aspect, the present invention relates to a method for imaging a sample on a substrate; the method comprising the steps of:
illuminating, at a first frequency using a modulated high intensity light source, the sample and the substrate, thereby causing the sample and the substrate to fluoresce;
capturing, at a second frequency using an image capturing device, both the sample fluorescence and the substrate fluorescence;
converting, using a frequency mixing process selected from a choice of two frequency mixing processes, both sample fluorescence and substrate fluorescence into low frequency signals, followed by processing, using a phase-resolving method dependent on the frequency mixing process, the low frequency signals to reduce the substrate fluorescence; and
visualising, using a display, a representation of the sample.

In another aspect, the present invention relates to an apparatus for a imaging a sample on a substrate, the apparatus comprising:
at least one modulated high intensity light source;
at least one modulator to modulate at least one lighting parameter of the at least one light source;
at least one image capturing device;
at least one controller for controlling at least one imaging parameter of the at least one image capturing device;
a first function generator for the at least one light source;
a second function generator for the at least one image capturing device;
at least one display;
at least one computer connected to, and controlling
the at least one light source,
the at least one modulator to modulate the at least one light source;
the at least one image capturing device;
the at least one controller for controlling the at least one image capturing device;
the first function generator for the at least one light source;
the second function generator for the at least one image capturing device; and the at least one display wherein
the at least one computer is capable of controlling the apparatus to effect a heterodyne or a homodyne phase-resolving process to obtain an image of the sample.

BRIEF DESCRIPTION OF THE DRAWINGS

FIGS. 6A to 6E are a series of graphs detailing the homodyne assisted phase-resolved method.

DETAILED DESCRIPTION OF THE DRAWINGS

It is an object of the present invention to enable the imaging of samples, particularly of latent fingerprints, on a larger range of substrate materials.

It is a further object of the present invention to overcome the problems associated with Laser-Induced-Fluorescence detection using the phase resolved method.

It is yet a further object of the present invention to use the phase resolved method to detect fluorescence emitted by latent fingerprints so that latent fingerprints can be visualised sufficiently clearly for forensic purposes.

A detailed description of the present invention will now be given in accordance with a preferred embodiment of the invention. In the following description, details are provided to describe the preferred embodiment. It shall be apparent to one skilled in the art, however, that the invention may be practiced without such details. Some of these details may not be described at length so as not to obscure the invention.

Figure 1:
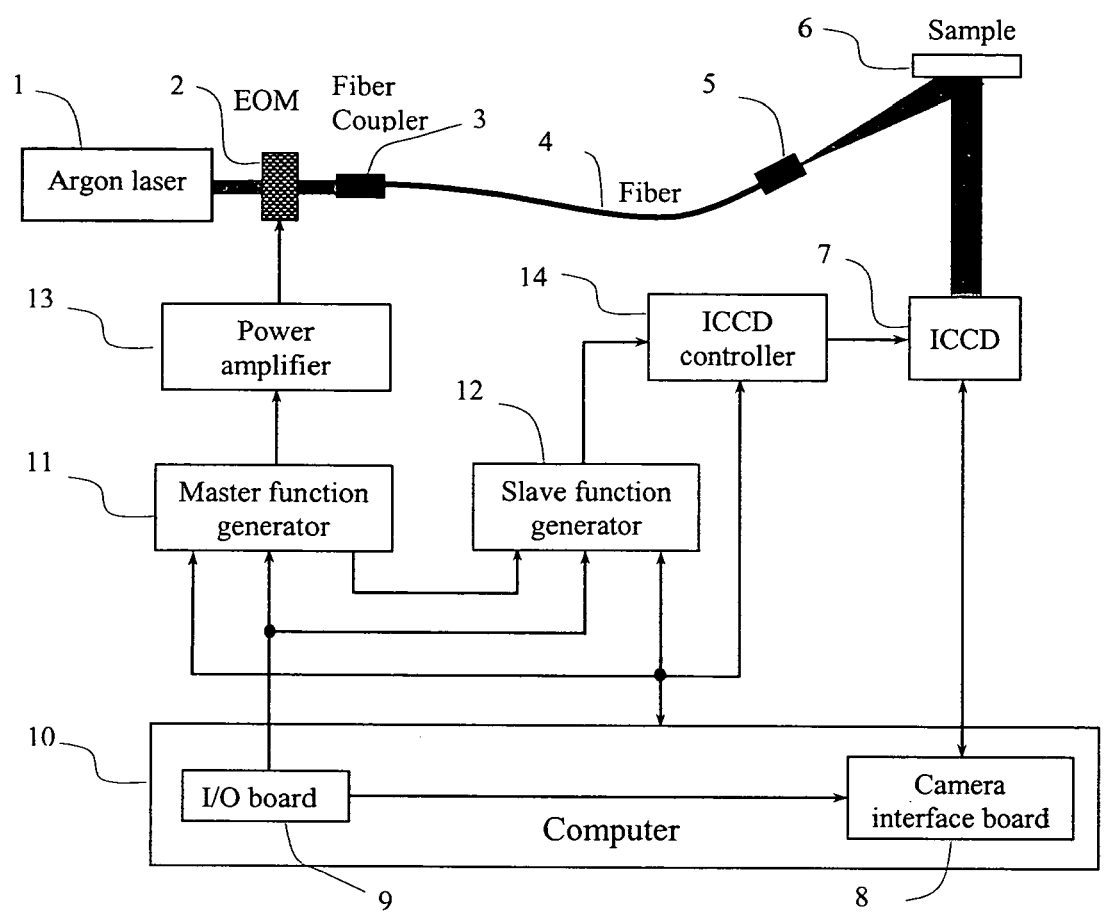
FIG. 1 shows a system diagram of the apparatus for the imaging of latent fingerprints under the present invention.

The system diagram as shown in FIG. 1 comprises an intensity modulated high intensity light source, such as a multi-line Argon laser 1 that is used as an excitation source for the sample 6. The parameters of the lighting source may be set at a predetermined profile, optimal for the nature of the sample. These parameters include the frequency of the light, the phase of the light and light intensity and are obtained from the combination of the following components.

The beam from the multi-line Argon laser 1 is incident on a modulator 2. Here, an Electro-Optical Modulator (EOM) capable of operating from 0 to 100 MHz is used. A power amplifier 13 is the power source of the EOM 2. The power amplifier is sinusoidally modulated by an output from a master function generator 11. The modulated laser beam from the EOM 2 is focused into a mode fibre 4 through a fibre coupler 3. The other end of the single mode fibre 4 is connected to a beam expander 5. The beam expander 5 illuminates the sample 6.

The fluorescent emissions from the sample 6, are collected by a suitable image capturing device such as Intensified Charge Coupled Device (ICCD) 7. The parameters of the image capturing device may also be set at a predetermined profile, optimal for the nature of the sample. These parameters include the frequency of image capture, the exposure time, the phase and gain amplitude. These parameters are obtained by adjusting the following components.

The ICCD comprises an Intensifier for magnifying the intensity levels of images it receives, and a Charge Coupled Device (CCD) for converting the intensified images from the Intensifier into digital images. The ICCD 7 is controlled by an ICCD controller 14 that provides voltage signals to drive the image intensifier in the ICCD. The gain of the ICCD 7 can be changed by varying the voltage signals to the intensifier. The voltage signals to the intensifier are also modulated by signals from a slave function generator 12.

The CCD camera in ICCD 7 is also connected to a camera interface board 8 and controlled by a computer 10. The computer 10 is also used to remotely control the master function generator 11, the slave function generator 12, and the ICCD controller 14 and other physical components of the invention. The master function generator 11, provides a clock reference to the slave function generator 12, synchronising the two function generators.

TABLE 1

Symbols and Notation

| Symbol | Meaning |
|---|---|
| A | Direct Current (DC) component of the modulated laser beam. |
| $A'(r_b)$ | DC component of the modulated fluorescence from the substrate. |
| $A'(r_f)$ | DC component of the modulated fluorescence from the fingerprint. |
| B | DC component of the modulated gain. |
| E(t) | Function of ICCD exposure control. |
| F(r,t) | Intensity signal of the modulated fluorescence from the sample. |
| G(t) | Signal of the modulated gain of the ICCD. |
| $H(r,t,\phi_g)$ | Mixing result of F(r,t) and G(t). |
| $H_O(r,\phi_g)$ | Image signals of homodyne mixing result. |
| $H_O(r,\phi_g)$ | Image signals of homodyne mixing result when setting $\phi_g = 0$. |
| $H_O(r,\pi/2)$ | Image signals of homodyne mixing result when setting $\phi_g = \pi/2$. |
| $H_O(r,\pi)$ | Image signals of homodyne mixing result when setting $\phi_g = \pi$. |
| $H_O(r,3\pi/2)$ | Image signals of homodyne mixing result when setting $\phi_g = 3\pi/2$. |
| $H_O(r,\phi_g)_{avg}$ | Average result of $H_O(r,0)$, $H_O(r,\pi/2)$, $H_O(r,\pi)$ and $H_O(r,3\pi/2)$. |
| I(t) | Intensity signal of the modulated laser beam. |
| k | Any integer. |
| K | A constant, which is proportional to the length of exposure time. |
| $m_b$ | Demodulation factor of the substrate fluorescence. |
| $m_{ex}$ | Modulation depth of the modulated laser beam. |
| $m_f$ | Demodulation factor of the fingerprint fluorescence. |
| $m_g$ | Modulation depth of the modulated gain. |
| r | Any position where fluorescence is excited from the sample. |
| $r_b$ | Position where the substrate fluorescence is excited. |
| $r_f$ | Position where the fingerprint fluorescence is excited. |
| $S_E(r,\phi_g)$ | Image signals after removing DC components when using heterodyne assisted phase-resolved method. |
| $S_O(r,\phi_g)$ | Image signals after removing DC components when using homodyne assisted phase-resolved method. |
| t | Time. |
| T | Length of the exposure time. |
| $\delta\omega$ | Frequency difference between the modulated laser beam and the modulated gain of the ICCD. |
| $\phi_b$ | Phase shift of the substrate fluorescence. |
| $\phi_f$ | Phase shift of the fingerprint fluorescence. |
| $\phi_g$ | Phase difference between two function generators. |
| $\tau_b$ | Lifetime of the substrate fluorescence. |
| $\tau_f$ | Lifetime of the fingerprint fluorescence. |
| $\omega_0$ | Angular frequency of the modulated laser beam. |
| $\omega_1$ | Angular frequency of the modulated gain of the ICCD. |

Figure 2:
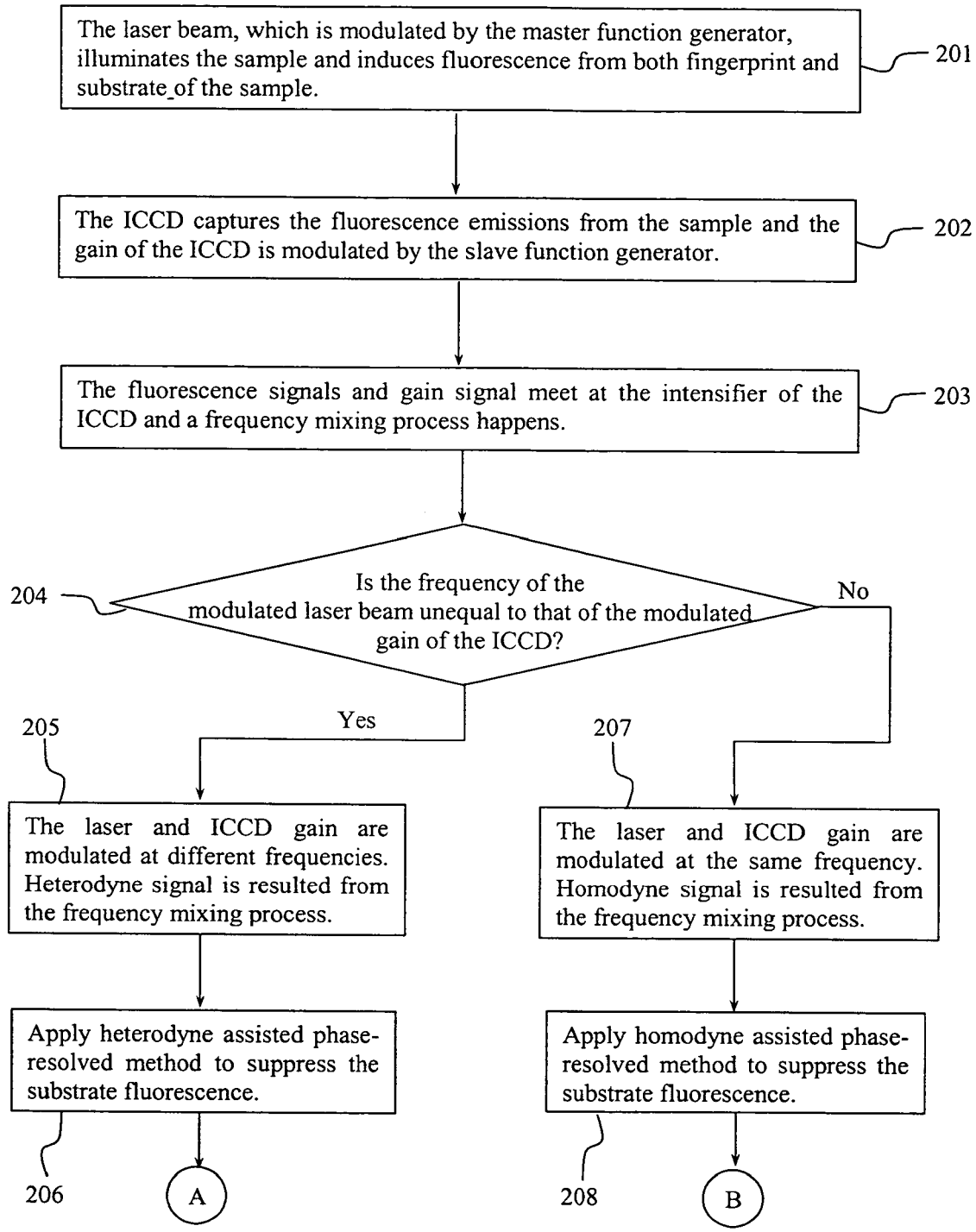
FIG. 2 shows a flow chart detailing the method for capturing fluorescence from the sample and subsrate.

As can be seen in FIG. 2 step 201, the modulated beam from the EOM 2, illuminates the sample 6. The modulated beam from the EOM 2 can be described as:

$$I(t) = A[1 + m_{ex}\sin(\omega_o t)] \quad (1)$$

Figure 4A:
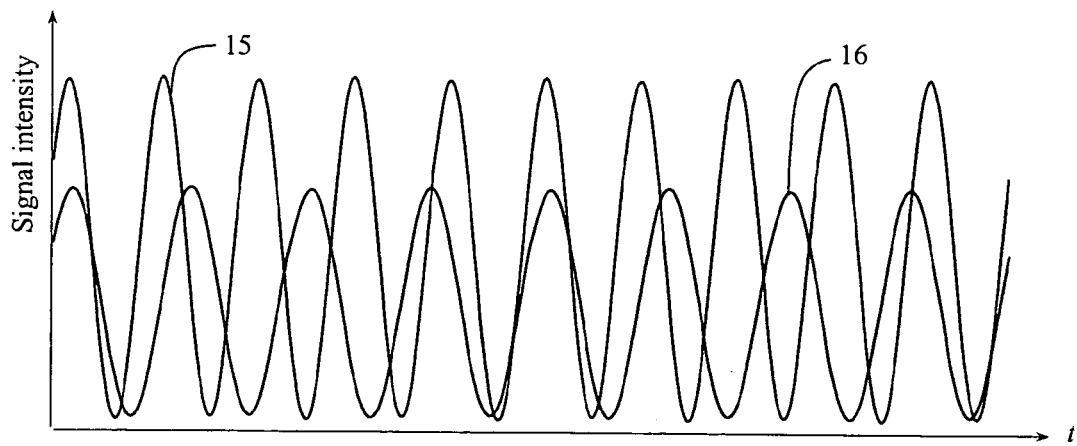
FIGS. 4A to 4H are a series of graphs detailing the heterodyne assisted phase-resolved method.

(as shown in curve 15 of FIG. 4A and FIG. 6A).

As a result of the illumination, the constituents within the fingerprint residue and the substrate of the forensic sample start to fluoresce upon illumination. The resulting fluorescence is modulated at the same frequency as that of the modulated excitation beam and of the expression:

$$F(r, t) = \begin{cases} A'(r_f)[1 + m_{ex}m_f\sin(\omega_0 t - \varphi_f)], & \text{when } r = r_f \\ A'(r_b)[1 + m_{ex}m_b\sin(\omega_0 t - \varphi_b)], & \text{when } r = r_b \end{cases} \quad (2)$$

Figure 4B:
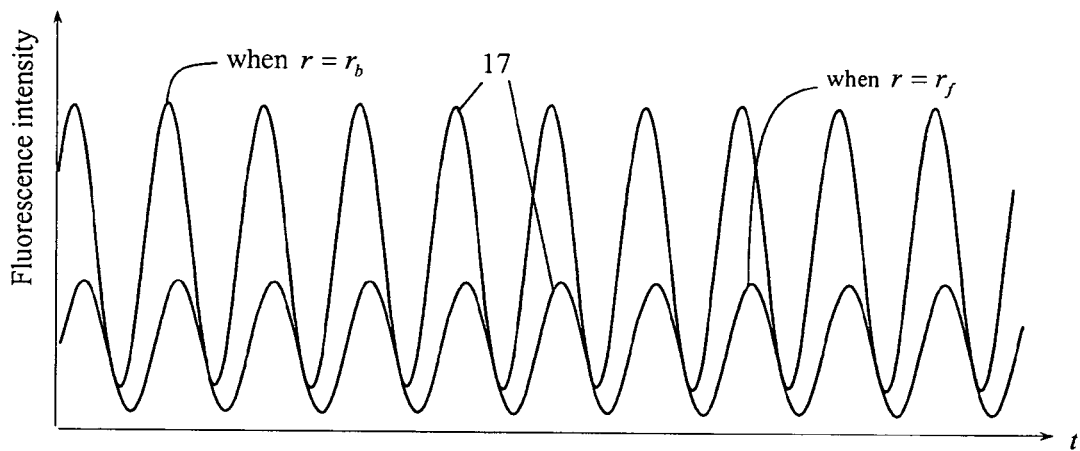

(as can be seen in curve 17 of FIG. 4B and FIG. 6B).

The fingerprint fluorescence and the substrate fluorescence are phase-shifted and demodulated to an extent determined by the fluorescence lifetime of the forensic sample. The phase-shift and demodulation factors are given by:

$$\begin{cases} \varphi_f = \text{arctg}(\omega_0 \tau_f) \\ m_f = [1 + (\omega_0 \tau_f)^2]^{-1/2} \end{cases} \quad (3)$$

$$\begin{cases} \varphi_b = \text{arctg}(\omega_0 \tau_b) \\ m_b = [1 + (\omega_0 \tau_b)^2]^{-1/2} \end{cases} \quad (4)$$

In step 202 (FIG. 2), the slave function generator 12 modulates the gain of the ICCD 7, with the modulated gain being of the form:

$$G(t) = B[1 + m_g \sin(\omega_1 t - \phi_g)] \quad (5)$$

(as can be seen in curves 16 and 23 of FIG. 4A and FIG. 6A).

In step 203, the modulated fluorescent emission signals meet and mix with the modulated gain of the ICCD 7 at the intensifier portion of the ICCD 7. This frequency mixing process generates a frequency mixing output, which is composed of a high frequency component and a low frequency component. The high frequency component is automatically filtered out by the CCD. This is because the CCD does not have a high frequency response; as such, all the high-frequency terms of the mixing output will be negated, leaving only the low frequency component. The mixing output is given by:

$$H(r, t, \varphi_g) = \quad (6)$$
$$\begin{cases} A'(r_f)B\left\{1 + \frac{1}{2}m_g m_{ex} m_f \cos[(\omega_0 - \omega_1)t - (\varphi_f - \varphi_g)]\right\}, & \text{when } r = r_f \\ A'(r_b)B\left\{1 + \frac{1}{2}m_g m_{ex} m_b \cos[(\omega_0 - \omega_1)t - (\varphi_b - \varphi_g)]\right\}, & \text{when } r = r_b \end{cases}$$

Figure 4C:
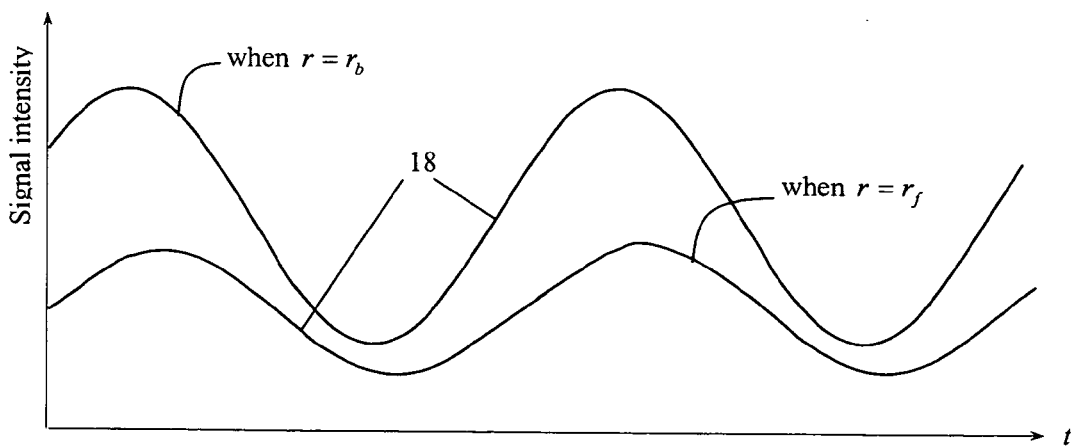

(as can be seen in curve 18 of FIG. 4C).

Step 204 is a decision step, which decides what the next signal processing process would be. This decision step depends on the frequency difference between the modulated laser beam and the modulated gain of the ICCD 7. If the angular frequency of the modulated laser beam is different from that of the modulated gain of the ICCD 7, a heterodyne signal results. If the angular frequency of the modulated laser beam is the same as the modulated gain of the ICCD 7, a homodyne signal results.

Consequently, in step 204, a decision will be made as to the phase-resolved method to be applied, branching either to a heterodyne assisted method (Steps 205 and 206) or a homodyne assisted method (Steps 207 and 208). Both the homodyne assisted phase-resolved method and the heterodyne assisted phase resolved method are for removing the contribution from the substrate fluorescence to generate clearer fingerprint images from the mixing output.

Figure 3:
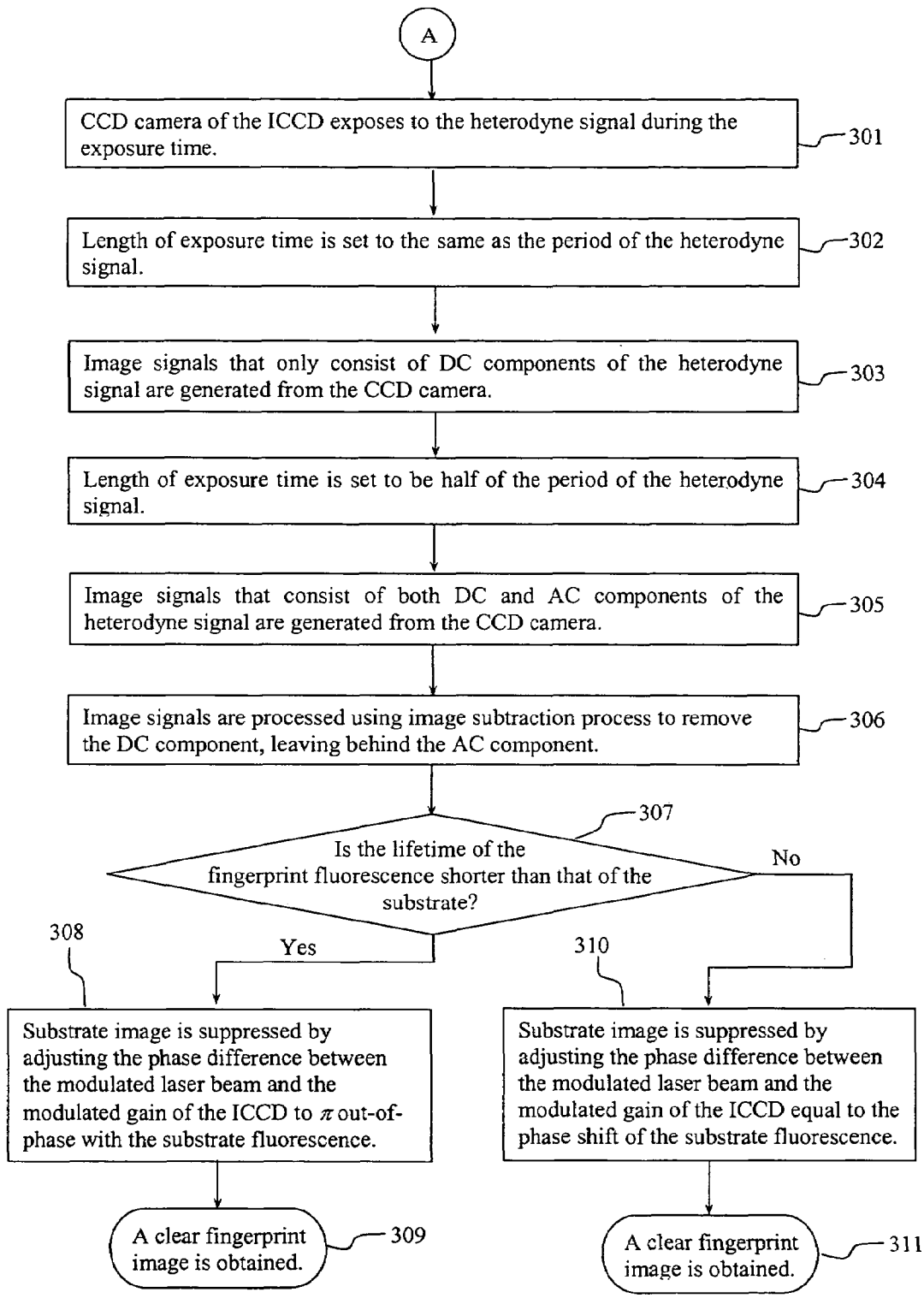
FIG. 3 shows a flow chart detailing the method for the heterodyne assisted phase-resolved method.

The heterodyne assisted phase-resolved method as shown in FIG. 3 requires the master function generator 11 and the slave function generator 12, to provide separate outputs at slightly differing frequencies. The multi-line Argon laser 1 and the gain of ICCD 7 are modulated at different frequencies and the phase difference between the two outputs can be adjusted from 0 to $2\pi$. The heterodyne frequency mixing process produces a low frequency heterodyne signal, which is the frequency difference between the master function generator 11 and the slave function generator 12, as described below:

$$H(r, t, \varphi_g) = \quad (7)$$
$$\begin{cases} A'(r_f)B\left\{1 + \frac{1}{2}m_g m_{ex} m_f \cos[(\omega_0 - \omega_1)t - (\varphi_f - \varphi_g)]\right\}, & \text{when } r = r_f \\ A'(r_b)B\left\{1 + \frac{1}{2}m_g m_{ex} m_b \cos[(\omega_0 - \omega_1)t - (\varphi_b - \varphi_g)]\right\}, & \text{when } r = r_b \end{cases}$$

(as can be seen in curve 18 of FIG. 4C).

The heterodyne signal, which is a signal generated by the intensifier of the ICCD 7, includes both Alternating Current (AC) and Direct Current (DC) components. Only the AC component contains the phase and is thus useful for further phase-sensitive detection of fingerprint fluorescence. Therefore, to obtain clear and identifiable fingerprint images, the DC component needs to be filtered out first in order to successfully suppress the contribution of the substrate fluorescence.

Besides the gain modulation of the ICCD 7, another parameter that is controlled is the "exposure time" in an "external trigger" mode. This parameter is controlled through the camera interface board 8. To enable the "external trigger" mode, an I/O board 9 is used to trigger the camera interface board 8. The length of the "exposure time" can be user defined through the computer 10. When operating in the "external trigger" mode, the CCD camera of the ICCD 7 will wait for an external trigger signal from the I/O board 9 to start its user defined "exposure time". Thus this exposure time can be described as a square wave function, where T is the length of exposure time:

$$E(t) = \begin{cases} 1 & 2kT \leq t < 2k+1)T \\ 0 & (2k+1)T \leq t < 2(k+1)T \end{cases}, \text{where } k = 0, 1, 2 \cdots \quad (8)$$

Figure 4D:
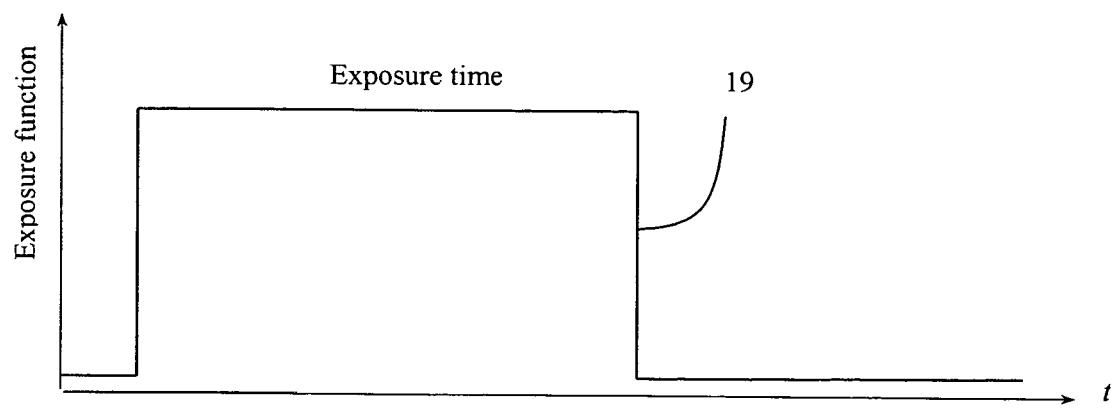
Figure 4E:
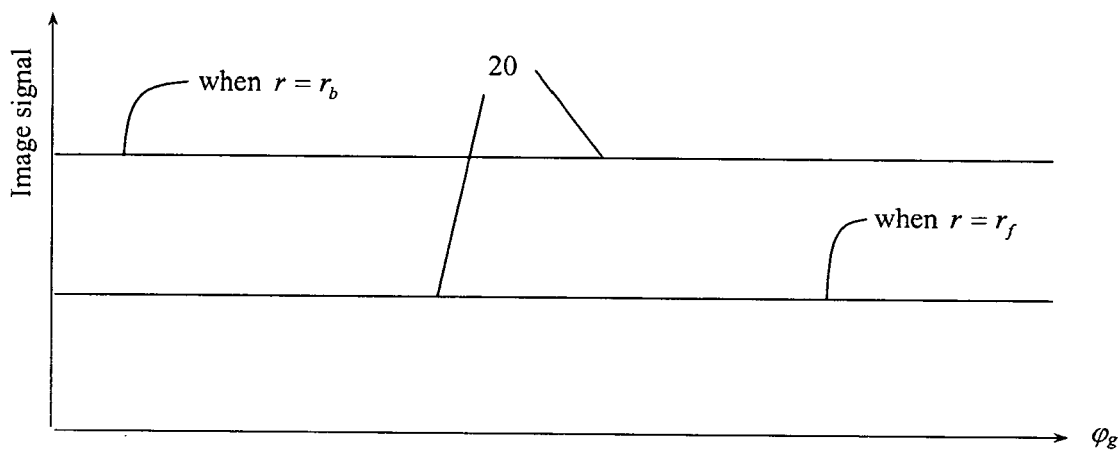
Figure 4F:
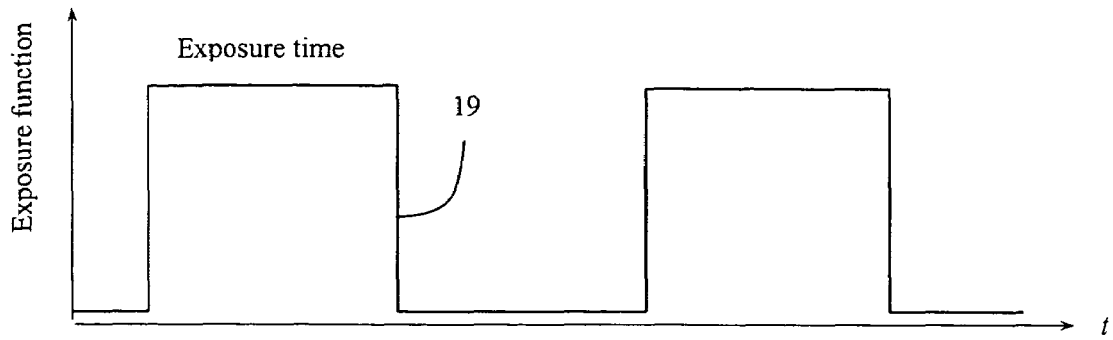

(as can be seen in curve 19 of FIG. 4F).

During this "exposure time", which acts as an "on" period of the square wave, the CCD camera in ICCD 7 will carry out an optical integration on the heterodyne signal and generate an image signal to the computer 10, as shown in step 301.

The I/O board 9 is also used to simultaneously trigger the master function generator 11 and the slave function generator 12.

By setting the length of "exposure time" the same as the period of the heterodyne signal as shown in step 302, (i.e. T=2π/δω), a first image signal that only consists of the DC component of the heterodyne signal is obtained, as shown in step 303. This can be expressed in the following function:

$$\int_0^{\frac{2\pi}{\delta\omega}} H(r, t, \varphi_g) dt = \begin{cases} \frac{2\pi}{\delta\omega} BA'(r_f), & \text{when } r = r_f \\ \frac{2\pi}{\delta\omega} BA'(r_b), & \text{when } r = r_b \end{cases} \quad (9)$$

(as can be seen in curve 20 of FIG. 4E).

Moreover, in step 304, by changing the length of "exposure time" to be half of the period of heterodyne signal (i.e. T=π/δω), a second image signal that consists of both the DC and AC components of the heterodyne signal is obtained as shown in step 305. This can be expressed by the following function:

$$\int_0^{\frac{\pi}{\delta\omega}} H(r, t, \varphi_g) dt = \qquad (10)$$

$$\begin{cases} \frac{\pi}{\delta\omega} BA'(r_f) + \frac{Bm_{ex}m_g}{\delta\omega} A'(r_f) m_f \sin(\varphi_f - \varphi_g), & \text{when } r = r_f \\ \frac{\pi}{\delta\omega} BA'(r_b) + \frac{Bm_{ex}m_g}{\delta\omega} A'(r_b) m_b \sin(\varphi_b - \varphi_g), & \text{when } r = r_b \end{cases}$$

Figure 4G:
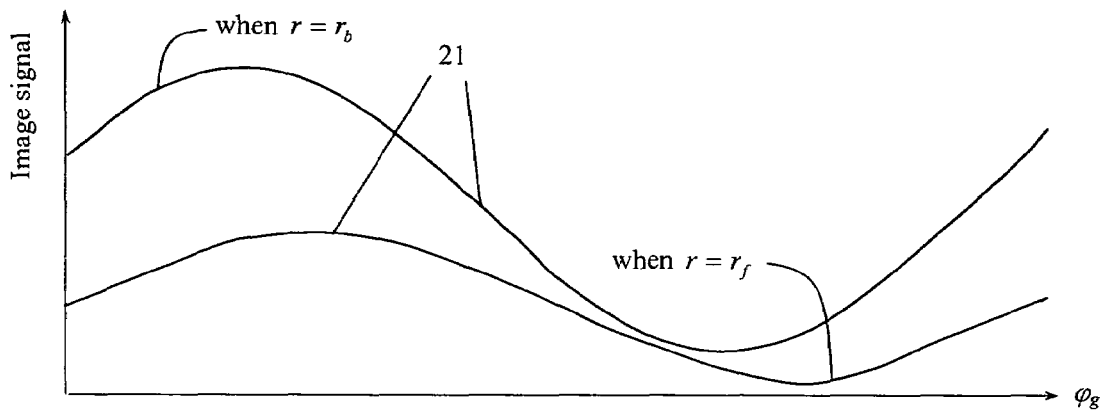

(as shown in curve 21 of FIG. 4G).

As shown in step 306, in order to obtain the AC component of the heterodyne signal, the first image signal is subtracted from the second image signal by mixing the signals using any suitable image subtraction process known in the art, to remove DC component. The resulting image signal has only the AC component of the heterodyne signal as can be seen in the following function:

$$S_E(r, \varphi_g) = \begin{cases} \frac{1}{\delta\omega} Bm_g m_{ex} A'(r_f) m_f \sin(\varphi_r - \varphi_g), & \text{when } r = r_f \\ \frac{1}{\delta\omega} Bm_g m_{ex} A'(r_b) m_b \sin(\varphi_b - \varphi_g), & \text{when } r = r_b \end{cases} \quad (11)$$

(as shown in curve 22 of FIG. 4).

Step 307 is a decision step as to whether the fluorescence lifetime of the substrate is greater than that of the fingerprint. If the fluorescence lifetime of the substrate is greater than that of the fingerprint, step 308 would be implemented. In step 308, the substrate fluorescence component is suppressed by adjusting the phase between the master function generator 11 and the slave function generator 12 to be π out-of-phase with the substrate fluorescence emission. Following this, a clear fingerprint image is obtained as shown in the concluding step 309. The suppression result is given by:

$$S_E(r, \varphi_g) = \begin{cases} \frac{1}{\delta\omega} Bm_g m_{ex} A'(r_f) m_f \sin(\varphi_b - \varphi_f), & \text{when } r = r_f \\ 0, & \text{when } r = r_b \end{cases} \quad (12a)$$

(when $\tau_f < \tau_b$, $\varphi_g = \varphi_b + \pi$)

Figure 4H:
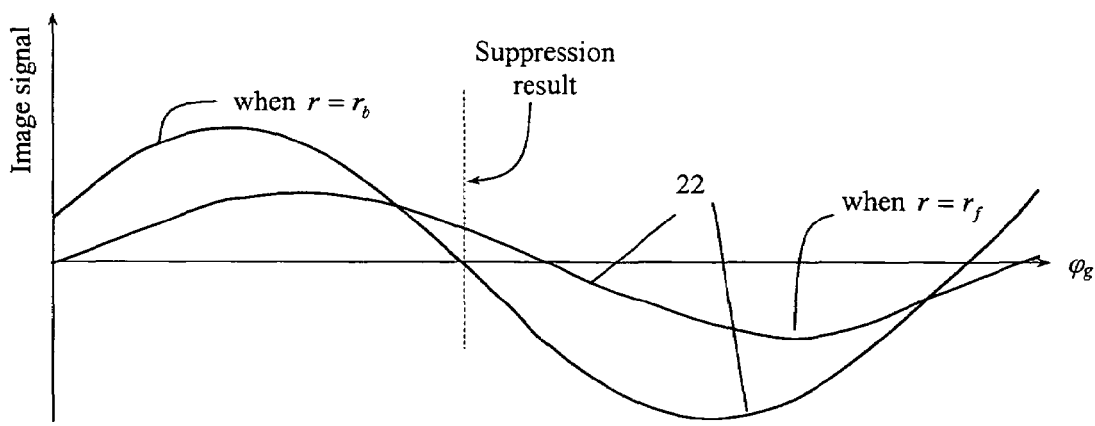

(shown as the position of "suppression result" in curve 22 of FIG. 4H).

If the fluorescence lifetime of the substrate is not greater than that of the fingerprint, step 310 would be implemented whereby the substrate fluorescence component is suppressed by adjusting the phase between the master function generator 11 and the slave function generator 12 to be in phase with the substrate fluorescence emission. Following this, a clear fingerprint image is obtained as shown in the concluding step 311. The suppression result is given by:

$$S_E(r, \varphi_g) = \qquad (12b)$$

$$\begin{cases} \frac{1}{\delta\omega} Bm_g m_{ex} A'(r_f) m_f \sin(\varphi_f - \varphi_b), & \text{when } r = r_f \\ 0, & \text{when } r = r_b \end{cases}$$

(when $\tau_f > \tau_b$, $\varphi_g = \varphi_b$)

(shown as the position of "suppression result" in curve 22 of FIG. 4H).

FIGS. 4A to 4H graphically represents the signal processing process of the heterodyne assisted phase-resolved method. Curve 15 and curve 16 of FIG. 4A respectively, show the modulation profiles of the excitation beam and the gain of the ICCD 7. As can be seen, curve 15 and curve 16 of FIG. 4A are of slightly different frequencies. Curve 17 of FIG. 4B provides an example of the fluorescence intensity from the latent fingerprint sample, consisting of fluorescence emissions from both the fingerprint and the substrate.

The fluorescence emissions have the same modulation frequency as that of the excitation but are demodulated and phase shifted to an extent determined by the respective fluorescence lifetimes. The frequency mixing process takes place when the modulated fluorescent emissions (as represented in curve 17 of FIG. 4B) combine with the modulated gain (as represented in curve 16 of FIG. 4) in the ICCD 7.

The result of the frequency mixing process is the heterodyne signal (as shown in curve 18 of FIG. 4C). The heterodyne signal consists of both the AC and DC components. Since only the AC component is wanted, the DC component is filtered out by controlling the exposure time of the ICCD 7. The profile of this exposure time is represented in curve 19 of FIG. 4D.

As shown in curve 19 of FIG. 4D, the start of the exposure time or the period of the curve 19 is switched "on", triggered at regular intervals. This period is in precise multiples of the period of the heterodyne signal (as shown in curve 18 of FIG. 4). At the "off" or non-exposure period, the CCD camera in the ICCD 7 does not receive any optical signals. The length of exposure time is user defined by the computer 10.

When the length of the exposure time of curve 19 of FIG. 4D is set the same as the period of that represented in curve 18 of FIG. 4C, the image signal that contains DC component only (as represented by the curve 20 of FIG. 4E), is obtained. When the length of the exposure time of curve 19 of FIG. 4D is set to one-half of the period (represented in curve 18 of FIG. 4C), an image signal that contains both AC and DC components (as represented by the curve 21 of FIG. 4G), is obtained.

Using a suitable image subtraction process, the DC component can be removed from the image signal (as shown in curve 22 of FIG. 4H). The contribution of the substrate fluorescence is suppressed by adjusting the phase between the master function generator 11 and the slave function generator 12 to either be $\pi$ out-of-phase or in phase with the substrate fluorescence emission. This depends on whether the fluorescence lifetime of the substrate is greater than that of the fingerprint, or not (as represented by the position of "suppression result" in curve 22 of FIG. 4).

Figure 5:
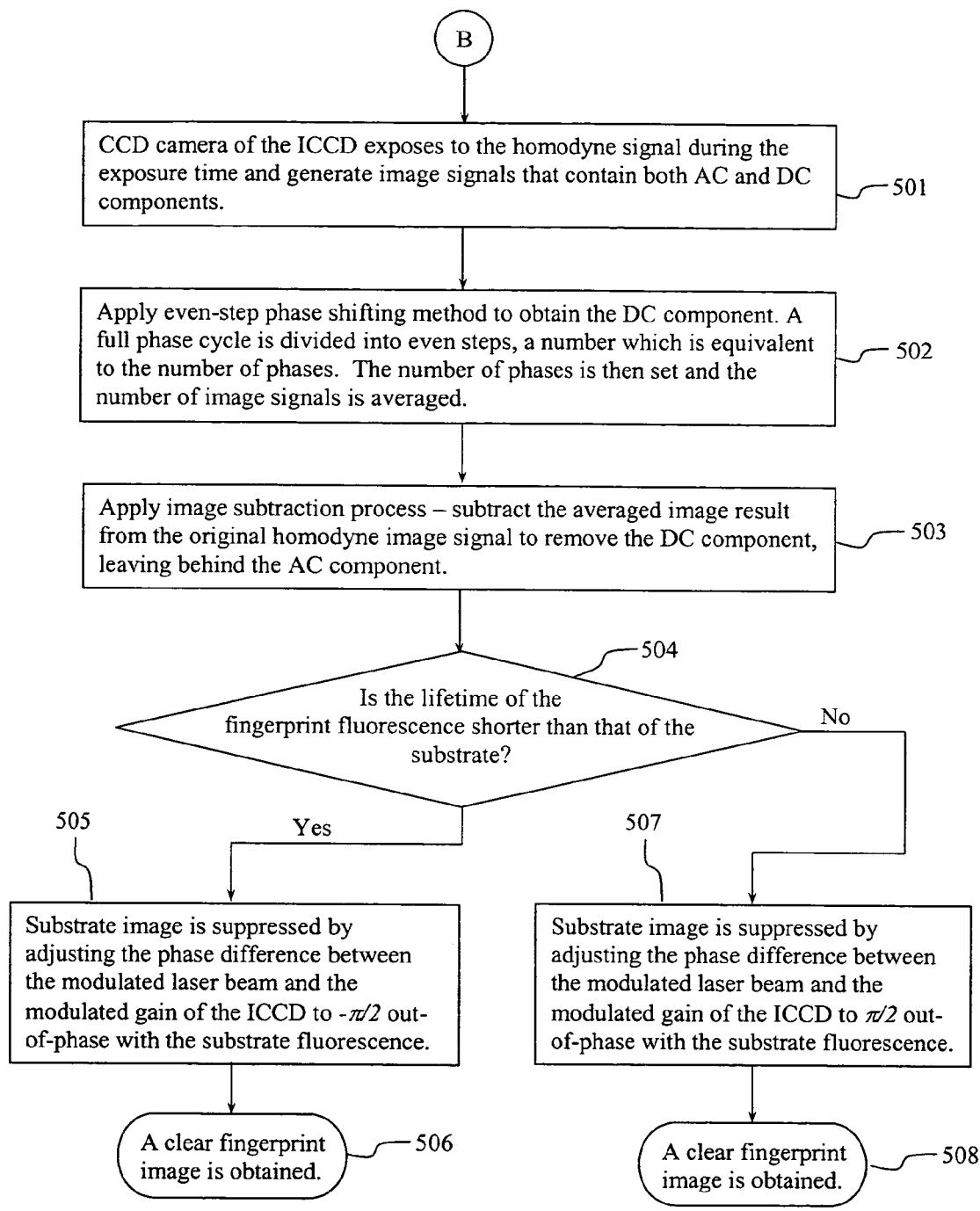
FIG. 5 shows a flow chart detailing the method for further fluorescence suppression using the homodyne assisted phase-resolved method.

The homodyne assisted phase-resolved method as shown in FIG. 5 requires the master function generator 11 and the slave function generator 12 to respectively provide separate outputs to the power amplifier 13 and the ICCD controller 14, at the same frequency. The multi-line Argon laser 1 and the gain of ICCD 7 are modulated at the same frequency, and the phase between the two outputs can be adjusted from 0 to $2\pi$.

As a result of frequency mixing, a homodyne signal that is time-independent is obtained in the ICCD 7. In step 501, the ICCD 7 carries out optical integration of the homodynesignal during its exposure period. Since the homodyne signal is time-independent, it is unnecessary to externally trigger the exposure time and therefore the resulting image signal is proportional to the homodyne signal. This is given by:

$$H_O(r, \varphi_g) = \begin{cases} KA'(r_f)B\left[1 + \frac{1}{2}m_g m_{ex} m_f \cos(\varphi_f - \varphi_g)\right], & \text{when } r = r_f \\ KA'(r_b)B\left[1 + \frac{1}{2}m_g m_{ex} m_b \cos(\varphi_b - \varphi_g)\right], & \text{when } r = r_b \end{cases} \quad (13)$$

(as can be seen in curve 24 of FIG. 6C).

Although the image signal is time-independent, it is still a function of the phase difference between the master function generator 11 and the slave function generators 12, with an additional DC component. As the DC component contains phase information which will corrupt the fingerprint image, the DC component needs to be filtered out.

In step 502, an even-step phase shifting method is used to determine the value of the DC component. The method starts by dividing a full phase cycle into an even number of steps equivalent to the number of phases required. The phase difference between the master function generator 11 and the slave function generator 12 is then set to the number of phases required. Based on the number of phases, there will be an equal number of image signals from the ICCD 7, and these image signals are then averaged. This phase shifting method is given by the expression:

$$H_O(r, 0) = \begin{cases} KA'(r_f)B\left(1 + \frac{1}{2}m_g m_{ex} m_f \cos\varphi_f\right), & \text{when } r = r_f \\ KA'(r_b)B\left(1 + \frac{1}{2}m_g m_{ex} m_b \cos\varphi_b\right), & \text{when } r = r_b \end{cases} \quad (14)$$

$$H_O(r, \pi/2) = \begin{cases} KA'(r_f)B\left[1 + \frac{1}{2}m_g m_{ex} m_f \cos(\varphi_f - \pi/2)\right], & \text{when } r = r_f \\ KA'(r_b)B\left[1 + \frac{1}{2}m_g m_{ex} m_b \cos(\varphi_b - \pi/2)\right], & \text{when } r = r_b \end{cases}$$

$$H_O(r, \pi) = \begin{cases} KA'(r_f)B\left[1 + \frac{1}{2}m_g m_{ex} m_f \cos(\varphi_f - \pi)\right], & \text{when } r = r_f \\ KA'(r_b)B\left[1 + \frac{1}{2}m_g m_{ex} m_b \cos(\varphi_b - \pi)\right], & \text{when } r = r_b \end{cases}$$

$$H_O(r, 3\pi/2) = \begin{cases} KA'(r_f)B\left[1 + \frac{1}{2}m_g m_{ex} m_f \cos(\varphi_f - 3\pi/2)\right], & \text{when } r = r_f \\ KA'(r_b)B\left[1 + \frac{1}{2}m_g m_{ex} m_b \cos(\varphi_b - 3\pi/2)\right], & \text{when } r = r_b \end{cases}$$

(shown as the four position $0, \pi/2, \pi, 3\pi/2$ in curve 24 of FIG. 6C).

The averaged result, which shows the value of DC component only, is expressed as:

$$H_O(r, \varphi_g)_{avg} = \begin{cases} KA'(r_f)B, & \text{when } r = r_f \\ KA'(r_b)B, & \text{when } r = r_b \end{cases} \quad (15)$$

Figure 6D:
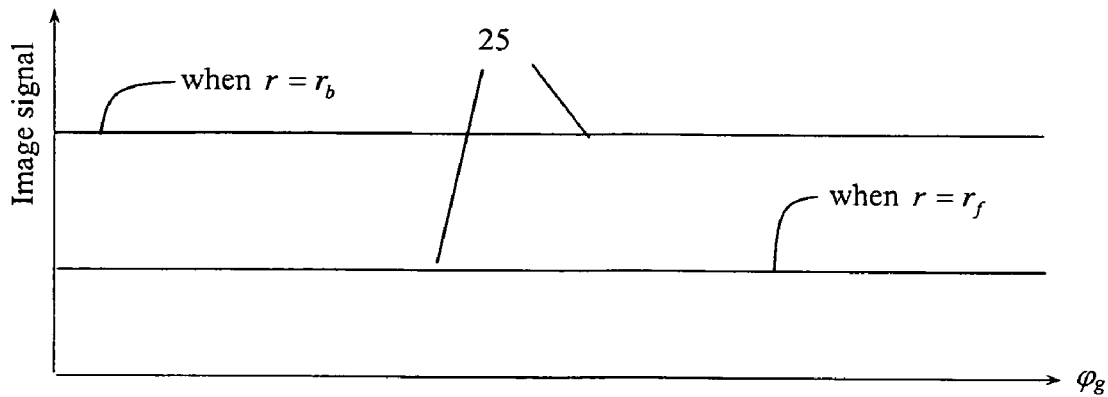

(as can be seen in curve 25 of FIG. 6D).

In step 503, the DC component is removed by mixing the average result with the original image signal and applying an image subtraction process, and the new image signal can be written as:

$$S_O(r, \varphi_g) = \begin{cases} \frac{1}{2}KB m_g m_{ex} A'(r_f) m_f \cos(\varphi_f - \varphi_g), & \text{when } r = r_f \\ \frac{1}{2}KB m_g m_{ex} A'(r_b) m_b \cos(\varphi_b - \varphi_g), & \text{when } r = r_b \end{cases} \quad (16)$$

Figure 6E:
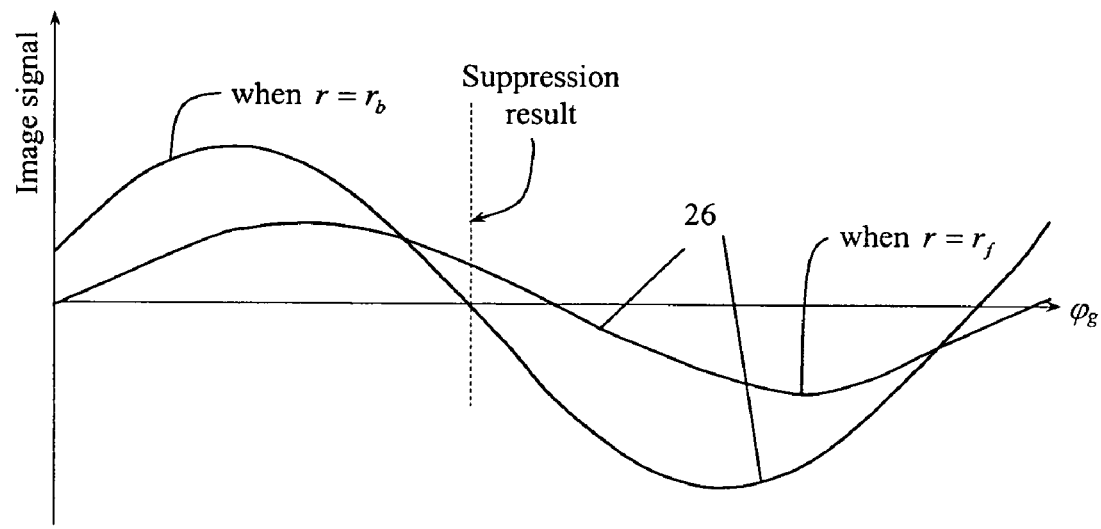

(as can be seen in curve 26 of FIG. 6E).

Step 504 is a decision step. If the fluorescence lifetime of the substrate is greater than that of the fingerprint, step 501 would be implemented and the substrate fluorescence is suppressed by adjusting the phase between the master function generator 11 and the slave function generator 12 to be $3\pi/2$ out-of-phase with the substrate fluorescence. Following this, a clear fingerprint image is obtained as shown in the concluding step 506. The suppression result is given by:

$$S_O(r, \varphi_g) = \begin{cases} \frac{1}{2}KBm_g m_{ex}A'(r_f)m_f \sin(\varphi_b - \varphi_f), & \text{when } r = r_f \\ 0, & \text{when } r = r_b \end{cases} \quad (17a)$$

$$(\text{when } \tau_f < \tau_b, \varphi_g = \varphi_b - \pi/2,)$$

(shown as the position of "suppression result" in curve 26 of FIG. 6E).

If the fluorescence lifetime of the substrate is not greater than that of the fingerprint, step 507 would be implemented and the substrate fluorescence is suppressed by adjusting the phase between the master function generator 11 and the slave function generator 12 to be in $\pi/2$ out-of-phase with the substrate fluorescence. Following this, a clear fingerprint image is obtained as shown in the concluding step 508. The suppression result is given by:

$$S_O(r, \varphi_g) = \begin{cases} \frac{1}{2}KBm_g m_{ex}A'(r_f)m_f \sin(\varphi_f - \varphi_b), & \text{when } r = r_f \\ 0, & \text{when } r = r_b \end{cases} \quad (17b)$$

$$(\text{when } \tau_f < \tau_b, \varphi_g = \varphi_b + \pi/2)$$

(shown as the position of "suppression result" in curve 26 of FIG. 6E).

FIGS. 6A to 6E graphically represents the signal processing process of the homodyne assisted phase-resolved method. Curve 15 and curve 23 of FIG. 6A respectively show the modulation profiles of the excitation beam and the gain of the ICCD 7. As can be seen, curve 15 and curve 23 of FIG. 6A are of identical frequencies. Curve 17 of FIG. 6B provides an example of the fluorescence intensity from the latent fingerprint sample, comprising fluorescence emissions from both sample and substrate. The fluorescence emissions have the same modulation frequency as that of the excitation, but are demodulated and phase shifted to an extent determined by the respective fluorescence lifetimes.

As can be seen, curve 24 of FIG. 6C is the image signal of the homodyne signal obtained from the ICCD 7. This image signal is a function of the phase difference between the master function generator 11 and the slave function generator 12. As the image signal contains the unwanted DC component, it needs to be filtered out using an even-step phase shifting method.

Curve 24 of FIG. 6C shows an example of the multi-step phase shifting method, the 4-step phase-shifting method, which divides a full phase cycle into four steps (shown as 0, $\pi/2$, $\pi$, $3\pi/2$ in curve 24 of FIG. 6C). Having set the phase difference between the master function generators 11 and the slave function generator 12 to the four phases and averaging the four corresponding image signals, the DC component is generated (as can be seen in curve 25 of FIG. 6).

Using any suitable image subtraction process known in the art, the DC component can be removed from the image signal (as shown in curve 26 of FIG. 6E). Consequently, any contribution from the fluorescence from the substrate can be suppressed by adjusting the phase between the master function generator 11 and the slave function generator 12 to either be $3\pi/2$ or $\pi/2$ out-of-phase with the substrate fluorescence emission. This choice depends on whether the fluorescence lifetime of the substrate is greater than that of the sample's (as represented by the position of "suppression result" in curve 26 of FIG. 6E).

While the foregoing has presented descriptions of certain preferred embodiments of the present invention, it is to be understood that these descriptions are presented by way of example only and are not intended to limit the scope of the present invention. It is expected that others skilled in the art will perceive variations which, while differing from the foregoing, do not depart from the spirit and scope of the invention as herein described and claimed.

A person skilled in the art will appreciate that other embodiments of the present embodiments may be used to visualise histological samples such as biological tissue on a microscope slide, as well as to visually detect the presence of biochemicals. The present invention uses novel and non-obvious means and techniques to overcome the problems of the art.

We claim:

1. A method for imaging a sample on a substrate, the method comprising the steps of:
    illuminating, at a first frequency using a modulated high intensity light source, the sample and the substrate, thereby causing the sample and the substrate to fluoresce;
    capturing, at a second frequency using an image capturing device, both the sample fluorescence and the substrate fluorescence;
    converting, using a frequency mixing process that comprises either a heterodyne process or a homodyne process, both sample fluorescence and substrate fluorescence into low frequency signals, followed by processing, using a phase-resolving method chosen in dependence on the frequency mixing process, the low frequency signals to reduce the substrate fluorescence; and
    visualising, using a display, a representation of the sample.

2. The method of claim 1, wherein the modulation of the high intensity light source comprises operating the high intensity light source at a predetermined profile, the predetermined parameter profile further comprising the first frequency, an initial phase and light intensity.

3. The method of claim 1, wherein the capturing of images by the image capturing device further comprises operating the image capturing device at a predetermined profile, the predetermined profile further comprising the second frequency, exposure time, phase and amplitude of gain.

4. The method of claim 1, wherein the frequency mixing process is selected based on a comparison between the first frequency to a modulated gain of the image capturing device.

5. The method of claim 1, wherein the frequency mixing processes is the heterodyne process, resulting from operating the high intensity light source and the image capturing device at different frequencies to obtain a low frequency heterodyne signal comprising alternating current (AC) and direct current (DC) components.

6. The method of claim 5, wherein the phase-resolving method comprises:
    setting exposure time of the image capturing device equal to the period of the heterodyne signal to generate a first image signal containing only the DC component, and setting exposure time of the image capture device to one half of the period of the heterodyne signal to generate a second image signal containing the DC and AC components; subtracting said first image signal from said second image signal to remove the DC component: and setting the phase of the high intensity light source and the phase of the image capturing device to be in phase with the substrate fluorescence when the lifetime of the substrate fluorescence is less or equal to the lifetime of the sample fluorescence, or $\pi$ out-of-phase with the substrate fluorescence when the lifetime of the substrate fluorescence is greater than the lifetime of the sample fluorescence, thereby reducing the substrate fluorescence.

7. The method of claim 1, wherein the frequency mixing processes is the homodyne process, resulting from operating the high intensity light source and the image capturing device at the same frequency to obtain a low frequency homodyne signal comprising alternating current (AC) and direct current (DC) components.

8. The method of claim 7, wherein the phase-resolving method comprises: dividing a full phase cycle ($2\pi$) of the high intensity light source and the image capturing device into an even plurality of intervals;

obtaining the an image signal for each one of said plurality of intervals;

averaging the image signals obtained, thereby obtaining a DC signal containing the DC component only; and subtracting the DC signal from the low frequency homodyne signal to remove the DC component.

9. The method of claim 1, comprising adjusting the phase difference between the high intensity light source and the image capturing device to reduce the contribution of the substrate fluorescence in the representation of the sample.

10. The method of claim 1, the method further comprises chemically treating the sample to enhance fluorescence.

11. The method of claim 1, wherein the sample is a latent forensic print of a body part.

12. The method of claim 11, wherein the body part is a finger.

13. The method of claim 1, wherein the sample is a histological sample.

14. The method of claim 1, wherein the sample is a biochemical sample.

15. An apparatus for a imaging a sample on a substrate, the apparatus comprising:

at least one modulated high intensity light source;

at least one modulator to modulate at least one lighting parameter of the at least one light source;

at least one image capturing device;

at least one controller for controlling at least one imaging parameter of the at least one image capturing device;

a first function generator for the at least one light source;

a second function generator for the at least one image capturing device;

at least one display; and at least one computer connected to, and controlling, the at least one light source, the at least one modulator to modulate the at least one light source, the at least one image capturing device, the at least one controller for controlling the at least one image capturing device, the first function generator for the at least one light source, the second function generator for the at least one image capturing device, and the at least one display, wherein the at least one computer is capable of controlling the apparatus to effect a heterodyne or a homodyne phase-resolving process to obtain an image of the sample.

16. The apparatus of claim 15, wherein the at least one modulated high intensity light source is capable of causing the sample to fluoresce.

17. The apparatus of claim 15, wherein the at least one modulated high intensity light source is an Argon laser.

18. The apparatus of claim 15, wherein the at least one modulator is capable of modulation from 0 to 100 MHz.

19. The apparatus of claim 15, wherein the at least one image capturing device is capable of having its gain modulated from 0 to 1 GHz.

20. The apparatus of claim 15, wherein the at least one image capturing device is capable of being externally triggered with an exposure time from 1 ms to 1,000 s.

21. The apparatus of claim 15, wherein the first function generator is capable of generating outputs of varying frequencies up to 1 GHz and phase differences from 0 to $2\pi$.

22. A method for imaging a sample on a substrate, comprising:

illuminating the sample and the substrate, using a modulated high intensity light source, thereby causing the sample and the substrate to fluoresce;

capturing sample fluorescence and substrate fluorescence, using an image capturing device;

converting the sample fluorescence and the substrate fluorescence into low frequency signals;

selecting a phase-resolving method depending on whether the low frequency signals are heterodyne signals or homodyne signals; and processing the low frequency signals, using the selected phase-resolving method, to produce an image signal with reduced contribution from the substrate fluorescence.

23. The method of claim 22, comprising removing a direct current (DC) component from the low frequency signal converted from the substrate fluorescence to produce a substrate signal comprising an alternating current (AC) component, and adjusting the phase difference between the high intensity light source and the image capturing device to suppress the substrate signal.

* * * * *

UNITED STATES PATENT AND TRADEMARK OFFICE
CERTIFICATE OF CORRECTION

PATENT NO. : 7,154,661 B2  Page 1 of 1
APPLICATION NO. : 11/023170
DATED : December 26, 2006
INVENTOR(S) : Leong Keey Seah et al.

It is certified that error appears in the above-identified patent and that said Letters Patent is hereby corrected as shown below:

TITLE PAGE
Item [75], line 2, replace "Vadake" with -- Vadakke --

COLUMN 5
Line 30, replace "$^{-1/2}$," with -- $^{-1/2}$. --

COLUMN 8
Line 20, replace "substrate" with -- substrate --

COLUMN 9
Line 54, replace "homodynesignal" with -- homodyne signal --

CLAIM 6
Col. 13, line 3, "subtracting" starts a new paragraph;
Line 5, replace ":" with -- ; --

CLAIM 8
Col. 13, line 25; delete "the"

Signed and Sealed this

Twenty-sixth Day of June, 2007

JON W. DUDAS
*Director of the United States Patent and Trademark Office*